US010898072B2

(12) United States Patent
Mantysalo et al.

(10) Patent No.: US 10,898,072 B2
(45) Date of Patent: Jan. 26, 2021

(54) METHOD AND SYSTEM FOR EVALUATING RELIABILITY OF RESULTS IN A VISUAL REACTION TEST

(71) Applicant: Ocuspecto Oy, Turku (FI)

(72) Inventors: Tapio Mantysalo, Hevonpaa (FI); Markku Leinonen, Turku (FI); Jaakko Suominen, Turku (FI); Iris Tigchelaar, Groningen (NL); Pekka Jarvinen, Turku (FI); Elias Maatta, Turku (FI); Kaisa Penttila, Helsinki (FI); Roope Kuutti, Turku (FI); Samuli Lahdenpera, Paimio (FI)

(73) Assignee: Ocuspecto Oy, Turku (FI)

( * ) Notice: Subject to any disclaimer, the term of this patent is extended or adjusted under 35 U.S.C. 154(b) by 0 days.

(21) Appl. No.: 16/956,901

(22) PCT Filed: Dec. 21, 2018

(86) PCT No.: PCT/FI2018/050964
§ 371 (c)(1),
(2) Date: Jun. 22, 2020

(87) PCT Pub. No.: WO2019/122533
PCT Pub. Date: Jun. 27, 2019

(65) Prior Publication Data
US 2020/0375450 A1    Dec. 3, 2020

(30) Foreign Application Priority Data

Dec. 22, 2017  (FI) .................................... 20170173

(51) Int. Cl.
A61B 13/00       (2006.01)
A61B 3/032       (2006.01)
A61B 3/00        (2006.01)
A61B 3/02        (2006.01)

(52) U.S. Cl.
CPC ............ *A61B 3/032* (2013.01); *A61B 3/0041* (2013.01); *A61B 3/02* (2013.01)

(58) Field of Classification Search
CPC .......... A61B 3/032; A61B 3/0041; A61B 3/02
(Continued)

(56) References Cited

U.S. PATENT DOCUMENTS 5,957,859 A     9/1999  Rosenfeld
6,497,576 B1 *  12/2002 Smith .................... A61B 5/162
                                                    128/897

(Continued)

FOREIGN PATENT DOCUMENTS

WO    93/08739 A1    5/1993
WO    00/78215 A1    12/2000
(Continued)

OTHER PUBLICATIONS

Search Report for Finnish patent appln. 20170173, Finnish Patent and Registration Office (dated Jul. 26, 2018).

*Primary Examiner* — William Choi
(74) *Attorney, Agent, or Firm* — James C. Lydon

(57) ABSTRACT

The invention relates to a method and a system for evaluating reliability of results in a visual reaction test taken by a user. Method steps with following phases are repeated several times:
A visual test stimulus with a recognisable value is shown to the user, at a stimulus time-point;
The user reports when she recognises the stimulus value, at a reporting time-point;
A variable and relatively short delay time is inserted between the visual stimuli;
Reaction times between the stimulus time-points and the reporting time-points are recorded;
Step times are calculated as a sum of the delay time and reaction time for each step.

(Continued)

Correlation between step times and delay times or correlation between reaction times and delay times is compared with predefined correlation values for reliability and thereby the level of reliability of the results is determined.

24 Claims, 6 Drawing Sheets

(58) Field of Classification Search
 USPC .............................. 600/558; 702/19; 434/236
 See application file for complete search history.

(56) References Cited

U.S. PATENT DOCUMENTS

| | | |
|---|---|---|
| 6,817,715 B2 | 11/2004 | Leinonen |
| D734,471 S | 7/2015 | Pollanen |
| 9,095,295 B2 | 8/2015 | Eagleman et al. |
| 9,456,740 B2 | 10/2016 | Leinonen et al. |
| 10,537,240 B2 | 1/2020 | Leinonen et al. |
| 2005/0143629 A1 | 6/2005 | Farwell |
| 2012/0271194 A1 | 10/2012 | MacLullich et al. |
| 2016/0022136 A1 | 1/2016 | Ettenhofer et al. |
| 2016/0220162 A1 | 8/2016 | Mantysalo et al. |
| 2016/0249798 A1 | 9/2016 | Mantysalo et al. |
| 2016/0262680 A1 | 9/2016 | Martucci et al. |

FOREIGN PATENT DOCUMENTS

| | | |
|---|---|---|
| WO | 2017004362 A1 | 1/2017 |
| WO | 2017/024845 A1 | 2/2017 |

* cited by examiner

METHOD AND SYSTEM FOR EVALUATING RELIABILITY OF RESULTS IN A VISUAL REACTION TEST

TECHNICAL FIELD OF THE INVENTION

The invention relates to a method and a system for evaluating reliability of results in a visual reaction test. The invention especially relates to a new way to determine whether a visual reaction test user is not fully attentive, is cheating or hasn't fully learned the operating principle of the test.

TECHNICAL BACKGROUND

Measuring the properties of human vision requires a cooperative test person in contrary to devices which assess the structure of the eye or visual system or measures electrical responses from the neural pathways. In vision measurements, a standardized visual stimulus is usually displayed to be detected or recognized by the test person. A response for the visual stimulus is usually given by the test person with a button or verbally. This response can be saved either manually or automatically and, depending of the response, a next stimulus (easier or more difficult) is presented.

This kind of methodology is called psychophysics. The most important part in this methodology is the properties of the visual stimulus, which must be designed in a way that it conforms to the theoretical frame of reference. In order to get accurate results from psychophysical measurements, another critical part is the cooperation of the test person: is she/he able to respond consistently based on the visual stimulus within reasonable time. In the case of dementia or cognitive impairment the cognitive performance can be so slow or variable, that it affects the accuracy of the measurements. Slow answers to the visual stimuli also diminishes the visual performance ability—you can't act as quickly based on the visual information compared to faster persons.

When a person is doing visual reaction time test, he/she should be fully attentive to the visual stimulus when it appears and responding only on the basis of the stimulus and not thinking something else and pressing the answering buttons in the rhythm which is not based on the appearance of the visual stimulus. This could happen e.g. when the person after head trauma is malingering or cheating and tries to deliberately get abnormally slow result in order to convince the insurance company that he has brain damage and suffers from traumatic brain injury. The person could have attentional difficulties which can result in concentration difficulties regarding the execution of the reaction time test. Problems arise also, if the person hasn't fully learned the principle of the test. In such cases the reaction time test would not measure reaction towards the visual stimulus.

U.S. Pat. No. 9,095,295 B2 presents a method for measuring the speed of visual perception of a user, WO 20171024845 A1 presents a stimulus information compiling method, US 2005/0143629 A1 and U.S. Pat. No. 5,957,859 present methods for detecting deception.

OBJECT OF THE INVENTION

It is an object of the present invention to reduce or even eliminate the above-mentioned problems appearing in prior art.

It is an object of the invention to achieve reliable results in a simple and easy-to-use visual reaction test.

It is an object of the invention an effective and simple way to determine whether a visual reaction test user is not fully attentive, is cheating or hasn't fully learned the operating principle of the test.

The present invention has especially an object of providing visual reaction time test where, in order to make judgements about the visual performance of a person, we are aware of cognitive reaction time to very basic and easy visual stimuli so that the limiting factor in testing is not the visual perception of the test stimulus—even in the case of defective visual system.

Terminology and Abbreviations

| | |
|---|---|
| Ocusweep device | Ocuspecto's unique multi-fixation perimeter, a Reaction-Time Perimeter |
| OcuRT test | Ocusweep Reaction Time test |
| RT or RealRT | Reaction time of a test step |
| DT | Delay Time of a test step |
| STP | Stimulus Time-Point of a test step |
| RTP | Reporting Time-Point of a test step |
| ST or StepTime | Step Time of a test step |
| ST/DT | correlation coefficient between the step time and the delay time of a step |
| RT/DT | correlation coefficient between the reaction time and the delay time of a step |

SUMMARY OF THE INVENTION

Among others, in order to realize the objects mentioned above, the method and the system for evaluating reliability of results in a visual reaction test, and other objects according to the invention, are characterized by what is presented in the enclosed independent claims.

The embodiments, examples and advantages mentioned in this text relate, where applicable, as well to method as to the system according to the invention, even though it is not always specifically mentioned.

A typical method according to the invention for evaluating reliability of results in a visual reaction test taken by a test user, comprises
starting the test;
repeating multiple test steps until a stop criterion is fulfilled, a single test step comprising following phases:
1) selecting a delay time of the step DT(Step), which is varied between steps;
2) not producing a visual test stimulus to be recognised for the delay time of the step DT(Step);
3) producing a visual test stimulus, at a stimulus time-point of the step STP(Step);
4) receiving, when reported by the user, the recognition of the stimulus, at a reporting time-point of the step RTP(Step);
5) beginning a new test step by returning to phase 1), until a stop criterion for the test is satisfied.
The method further comprises:
calculating:
reaction time of a step RT(Step) as time elapsed between the stimulus time-point of the step and the reporting time-point of the step, i.e. RT(Step)=RTP(Step)-STP(Step) and
step time of a step ST(Step) as sum of the delay time of the step and the reaction time of the step, i.e. ST(Step)=DT(Step)+RT(Step);

determining correlation between step times and delay times or correlation between reaction times and delay times of each test step;
comparing the correlation with predefined correlation values for reliability and thereby determining level of reliability of the results and consistency of test subject's responses.

One way to describe the invention is to define that the invention relates to a method and a system for evaluating reliability of results in a visual reaction test taken by a user. Method steps with following phases are repeated several times:

A visual test stimulus with a recognisable value is shown to the user, at a stimulus time-point;
The user reports when she recognises the stimulus value, at a reporting time-point;
A variable and relatively short delay time is inserted between the visual stimuli;
Reaction times between the stimulus time-points and the reporting time-points are recorded;
Step times are calculated as a sum of the delay time and reaction time for each step.

Correlation between step times and delay times or correlation between reaction times and delay times is compared with predefined correlation values for reliability and thereby the level of reliability of the results is determined.

In an embodiment of the invention the method comprises:
determining correlation between step times and delay times and correlation between reaction times and delay times of each test step;
comparing the determined correlations with predefined correlation values for reliability and thereby determining level of reliability of the results and consistency of test subject's responses.

It has thus been found, that for ensuring whether the person actually is reacting to the appearing of the visual stimulus, a variable and relatively short delay time can be inserted before the visual stimulus appears.

If the person is fully attentive to the visual stimulus appearance, his/her reaction time RT is not affected by the length of the delay. In this case the source of the variability of one step time ST is due to the variability of the delay time DT, i.e. there is a statistical relationship between the two variables. Therefore, the corresponding correlation coefficient ST/DT is high.

TABLE 1

A simulated reaction time test case, where the test subject is attentive and therefore answers consistently in 400 milliseconds after being presented with the stimulus. This results in a perfect correlation between DT and ST. Variance (RT) and variance (RT)/variance (DT) are both zero. All of these indicate reliable test results. All time units are in milliseconds. Population variance and Pearson correlation were used in calculations.

| Delay (DT) | ReactionTime (RT) | StepTime (ST) |
|---|---|---|
| 100 | 400 | 500 |
| 400 | 400 | 800 |
| 100 | 400 | 500 |
| 400 | 400 | 800 |
| 100 | 400 | 500 |
| 400 | 400 | 800 |
| 100 | 400 | 500 |
| 400 | 400 | 800 |
| 150 | 400 | 550 |
| 500 | 400 | 900 |
| 150 | 400 | 550 |
| 500 | 400 | 900 |
| 150 | 400 | 550 |

TABLE 1-continued

A simulated reaction time test case, where the test subject is attentive and therefore answers consistently in 400 milliseconds after being presented with the stimulus. This results in a perfect correlation between DT and ST. Variance (RT) and variance (RT)/variance (DT) are both zero. All of these indicate reliable test results. All time units are in milliseconds. Population variance and Pearson correlation were used in calculations.

| 500 | 400 | 900 |
|---|---|---|
| 150 | 400 | 550 |
| 500 | 400 | 900 |

| Correlation (DT, ST) | 1.00 |
|---|---|
| Variance (DT) | 27968.75 |
| Variance (RT) | 0.00 |
| Variance (RT)/Variance (DT) | 0.00 |

If the person is not fully attentive to the visual stimulus and is thinking about something else—maybe malingering or cheating, or hasn't fully learned the principle of the test—he/she tends to press buttons in a constant rhythm, while ignoring the length of the delay. Then the correlation coefficient ST/DT is low.

TABLE 2

A simulated reaction time test case, where a test subject is not fully attentive and answers otherwise consistently, except for a single sneeze or other distraction in the middle of the test (2 × 900 ms in RT column). This causes the calculated variance to increase substantially to the point, where the test can be considered unreliable. The same applies to variance (RT)/Variance (DT). However, correlation indicates a reliable test case because of the fairly linear relationship between DT and ST, and is therefore a more robust method against isolated mistakes. All time units are in milliseconds. Population variance and Pearson correlation were used in calculations.

| Delay (DT) | ReactionTime (RT) | StepTime (ST) |
|---|---|---|
| 100 | 400 | 500 |
| 400 | 400 | 800 |
| 100 | 400 | 500 |
| 400 | 400 | 800 |
| 100 | 400 | 500 |
| 400 | 400 | 800 |
| 100 | 400 | 500 |
| 400 | 900 | 1300 |
| 150 | 900 | 1050 |
| 500 | 400 | 900 |
| 150 | 400 | 550 |
| 500 | 400 | 900 |
| 150 | 400 | 550 |
| 500 | 400 | 900 |
| 150 | 400 | 550 |
| 500 | 400 | 900 |

| Correlation (DT, ST) | 0.70 |
|---|---|
| Variance (DT) | 27968.75 |
| Variance (RT) | 27343.75 |
| Variance (RT)/Variance (DT) | 0.98 |

TABLE 3

A simulated reaction time case, where a test subject tries to cheat by answering at regular intervals which are not based on the appearing of the stimulus. This results in a nonexistent correlation (DT, ST) and high variance (RT) and variance (RT)/variance (DT). These indicate unreliable test results. All time units are in milliseconds. Population variance and Pearson correlation were used in calculations.

| Delay (DT) | ReactionTime (RT) | StepTime (ST) |
|---|---|---|
| 100 | 800 | 900 |
| 400 | 500 | 900 |

TABLE 3-continued

A simulated reaction time case, where a test subject tries to cheat by answering at regular intervals which are not based on the appearing of the stimulus. This results in a nonexistent correlation (DT, ST) and high variance (RT) and variance (RT)/variance (DT). These indicate unreliable test results. All time units are in milliseconds. Population variance and Pearson correlation were used in calculations.

| | | |
|---|---|---|
| 100 | 800 | 900 |
| 400 | 500 | 900 |
| 100 | 800 | 900 |
| 400 | 500 | 900 |
| 100 | 800 | 900 |
| 400 | 500 | 900 |
| 150 | 750 | 900 |
| 500 | 400 | 900 |
| 150 | 750 | 900 |
| 500 | 400 | 900 |
| 150 | 750 | 900 |
| 500 | 400 | 900 |
| 150 | 750 | 900 |
| 500 | 400 | 900 |

| | |
|---|---|
| Correlation (DT, ST) | 0.00 |
| Variance (DT) | 27968.75 |
| Variance (RT) | 27968.75 |
| Variance (RT)/Variance (DT) | 1.00 |

TABLE 4

A simulated reaction time case, where the test subject is learning how to do the test, and getting faster towards the end of the test. Test subjects reaction time becomes steady between 400-500 milliseconds at the latter half of the test indicating that he/she has learned the test. As the RT becomes faster during the test, variance (RT) and variance (RT)/variance (DT) are high, and suggest that the test is unreliable. However, correlation indicates a reliable test case because of the fairly linear relationship between DT and ST. All time units are in milliseconds. Population variance and Pearson correlation were used in calculations.

| Delay (DT) | ReactionTime (RT) | StepTime (ST) |
|---|---|---|
| 100 | 850 | 950 |
| 400 | 810 | 1210 |
| 100 | 770 | 870 |
| 400 | 730 | 1130 |
| 100 | 690 | 790 |
| 400 | 650 | 1050 |
| 100 | 610 | 710 |
| 400 | 570 | 970 |
| 150 | 530 | 680 |
| 500 | 490 | 990 |
| 150 | 450 | 600 |
| 500 | 440 | 940 |
| 150 | 420 | 570 |
| 500 | 480 | 980 |
| 150 | 430 | 580 |
| 500 | 460 | 960 |

| | |
|---|---|
| Correlation (DT, ST) | 0.70 |
| Variance (DT) | 27968.75 |
| Variance (RT) | 20085.94 |
| Variance (RT)/Variance (DT) | 0.72 |

The determining of the level of reliability of the results can also be done by comparing the variability of reaction time RT against the variability of the delay time DT, i.e. there is a statistical relationship between the two variables. A corresponding correlation coefficient RT/DT may be determined.

In an embodiment the method comprises: determining, for such steps where the stimulus was correctly recognised, a correlation coefficient ST/DT between the step time and the delay time of the step; and comparing the calculated correlation coefficients ST/DT with predefined values for reliability and thereby determining level of reliability of the results.

The reliability of the measurement can thus be judged by the correlation coefficient ST/DT or RT/DT. If the correlation is high enough, the measurement can be considered reliable.

The correlation may mean any statistical association. In an embodiment the correlation refers to how close the variables are to having a linear relationship with each other, i.e. a linear correlation. An embodiment of the invention uses Pearson correlation coefficient. In an embodiment the correlation refers to a non-linear correlation. An embodiment uses a rank correlation such as Spearman's rank correlation coefficient or Kendall's rank correlation coefficient. In an embodiment the correlation refers to any mathematical function derived from DT and RT, or DT and ST, or RT and ST.

In order to find the predefined correlation values for reliability, i.e. cut off values for reliable measurements, the correlation coefficient can be studied in repeated measurements within one test user to find out the effect of learning. Also, the correlation coefficient can be studied among persons skilled in the test and comparing their results to results achieved during added cognitive load and deliberate malingering or cheating.

In an embodiment of the invention a fake stimulus or another stimulus not meant to be recognised in the test during the delay time of the step is provided. This kind of stimulus is meant e.g. to test if the test user is fully attending to the test.

In an embodiment the correlations are calculated from a limited set of steps. They can be calculated e.g. from only those steps where the stimulus was correctly recognized, or from only those where reaction time RT(Step) or step time ST(Step) or delay time DT(Step) fulfils specific criteria.

In an embodiment reliability of responses during the test, or during a subset of test steps, is further determined by number of incorrect answers in relation to correct answers.

In an embodiment, in order to reach a better test—retest repeatability, the reported actual reaction time RT of the test subject is determined by using the fastest subset segment of test steps e.g. by dividing the step series to sub-blocks and selecting the fastest reliable sub-block. The fastest means e.g. the test or segment of tests or sub-block of tests which the test user responded acceptably in the shortest time.

In an embodiment the method comprises:
determining for all test steps or for any subset of test steps, a correlation coefficient ST/DT(Step) between the step time and the delay time of the step;
comparing the calculated correlation coefficients with predefined values for reliability and thereby determining level of reliability of the results and consistency of test subject's responses.

In an embodiment of the invention the produced visual test stimulus has a property that has a visually recognizable value. The test user must concentrate at least somewhat in order recognize the value. When the user recognises the value she/he reports it e.g. with a reporting device.

The delay time of the step may be varied randomly or by any predefined sequence or by an algorithm between a lower limit and a higher limit of the delay time. The lower limit and/or the higher limit maybe changed between test steps. This may be done according to reaction times of the user or according to other predefined criteria. If the user is slow, the lower and higher limit may be increased. If the user has fast reactions, the lower and higher limit may be decreased.

In an embodiment the lower limit is selected to be between 50 and 500 ms or between 65 and 200 ms. In an embodiment the higher limit is selected to be between 200 and 1000 ms or between 250 and 800 ms.

In an embodiment the reporting by the user is done by pressing a reporting button. In an embodiment of the invention the value of the stimulus property is selected from a group of at least two different values. The button may be selected from a group of at least two different reporting buttons, whereby each button is associated with one possible value of the stimulus property.

The visual test stimulus may comprise a symbol having a visually recognizable value indicating a direction, such as an arrow or a standard Landot-C. In an embodiment said group of at least two different values comprises values "left" and "right". These are simple and reliable symbols and values.

In an embodiment the test user reports the visual test stimulus or value of the visual test stimulus property, such as stimulus direction, by push-buttons, touch elements, moves of body or body parts, eye movements, oral feedback, magnetic or electrical signal from brain or neural system.

In an embodiment, the test user's incorrect recognitions of the visual test stimulus or value of a visual test stimulus property produce a wrong response feedback or sign for the test user, indicating wrong response, thus encouraging to respond correctly. The feedback may also be a sound, a vibration, or a light or any combination of them.

In an embodiment of the invention the visual test stimulus is producing on an electronic screen. In an embodiment, the visual test stimuli may be shown on somewhat different locations on the screen. Especially, if a stimulus was correctly recognised, the next visual test stimulus may be produced on a different location on the screen.

In an embodiment of the invention the stop criterion is defined to be satisfied when a number of successive steps where the stimulus was correctly recognised is recorded. That number may be e.g. from 3 to 10, from 4 to 8 or from 5 to 7.

In an embodiment of the invention reaction times of steps with shorter delays are summed, averaged, or otherwise bundled together as RT(ShortDelays). Separately of that, reaction times of steps with longer delays than the ones bundled to RT(ShortDelays) are summed, averaged, or otherwise bundled together as RT(LongDelays). The absolute values of the RT(ShortDelays) and RT(LongDelays) or difference or relation of these are used to further analysis. They may be used e.g. to determine how well the concentration of the test user recovers from reporting task of the previous step, using a relation between RT(ShortDelays) and RT(LongDelays), or to determine what is the reaction time without impact of previous step, i.e. RT(LongDelays).

In an embodiment the invention can be used to determine the minimum time a person needs for recovery from a previous step in order to be attentive to the new stimulus. This is done by shortening the delay until reaction time begins to slow down.

The invention may be realised as a system for evaluating reliability of results in a visual reaction test taken by a user. Such a system comprises
 a computer with a memory;
 a computer program runnable on the memory, the program comprising program code elements adapted to perform and control the visual reaction test;
 a display device arranged show a visual test stimulus as instructed by the computer program;
 a reporting device arranged to receive a recognition of the stimulus by the user and arranged to transfer information of said recognition to the computer.

The system, especially its computer program with program code elements is adapted to perform the method steps according to embodiments mentioned in this text.

BRIEF DESCRIPTION OF THE FIGURES

The invention is described in more detail below with reference to the enclosed schematic drawing, in which.

DETAILED DESCRIPTION OF THE EXAMPLES

Example 1: Ocusweep Reaction Time Test (OcuRT Test)

In order to find the cut off value for a reliable measurement, we studied the correlation coefficient in repeated measurements within one test subject to find out the effect of learning. Also, we compared the correlation coefficient among persons skilled in the test to results achieved during added cognitive load and deliberate malingering or cheating.

The test subjects were seated in front of an Ocusweep device and an Ocusweep tablet at a close distance, and an Ocusweep remote control was handed to them. In the test, the tablet displayed a series of black rings, which have an opening on the left or on the right side. The test subjects were advised to push either the left or right button of the remote control, depending on which side the opening was located, and they were told to do this as quickly as possible. They were also instructed not to guess and only answer when they see the opening. As a result of a wrong answer, a red circle appeared on the tablet, which disappeared after correct button press. The next symbol was displayed but only after a random delay period of 100 ms to 400-560 ms, depending on the personal reaction time of the subject. After three rounds (called OcuRT1, OcuRT2, OcuRT3), the test terminated, and the shortest median reaction time of six consecutive correct answers was calculated and displayed on the tablet screen.

In a variation of this test, denoted "cognitive load", the test subjects were told to count down from 200 by 7's while they were doing the reaction time test. They were instructed not to count between rounds, and start counting again when a new round starts. The test subjects were also told to start counting again from 200, if they forget the number they were counting from in the middle of the test, or if they reach zero.

In another variation, denoted "cheat", the test subjects were told to have the following mindset: Imagine, that you have bumped your head and you are going to the doctor to test your reaction time. However, you want to get some money from your insurance company, and deliberately answer slowly, as if the head trauma had affected your reaction time. To sum up, you should answer slowly but in a plausible way, to cheat money out of the insurance company.

The reliability of the OcuRT measurements were classified with the help of the correlation coefficient ST/DT. If the person is fully attending to the visual stimulus' appearance, the reaction time is not affected by the variability of the random delay but the variability can be detected in the total step time causing high correlation values.

Figure 1:
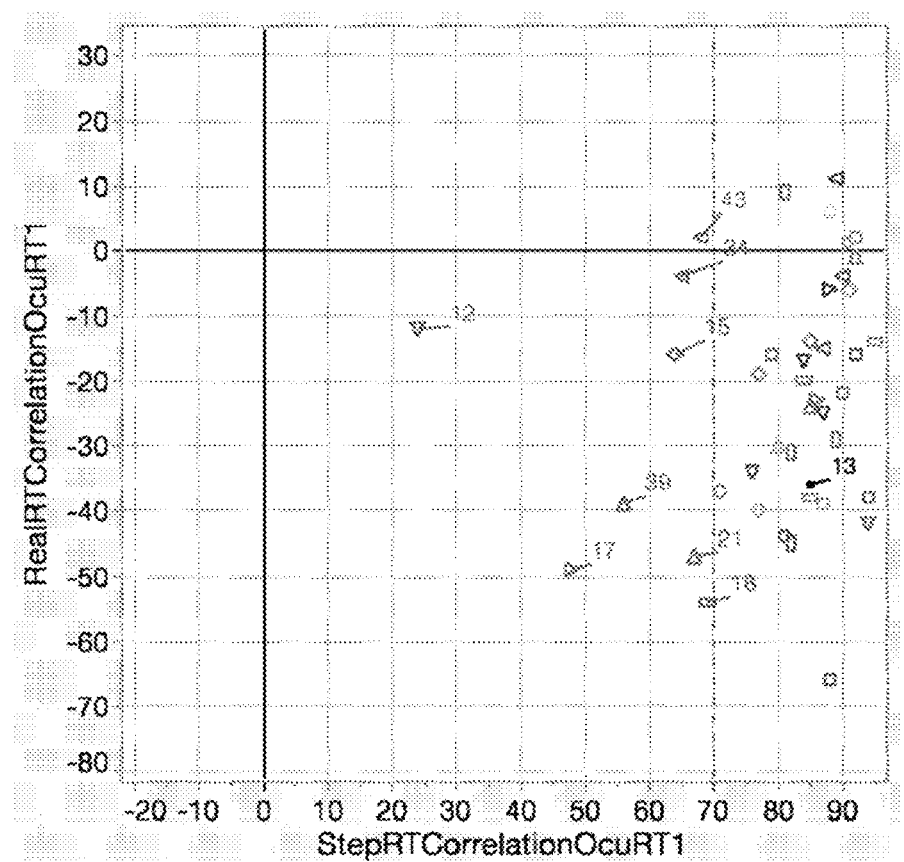
FIG. 1 shows correlations of StepTime of the first OcuRT measurement OcuRT1.

FIG. 1 shows correlation coefficient of the delay of the first OcuRT measurement OcuRT1 of each test subjects (n=44) against the total step time ST (marked here as StepTime, x-axis) and individual reaction time RT (RealRT, y-axis). Test subjects with legend are showing correlation below 70% against StepTime which means that the persons are not fully attending to the visual stimulus appearance—maybe because of concentrating to other thoughts or not fully mastering the OcuRT test. Subject number 13 couldn't do the test because of discomfort glare caused by the tablet.

Figure 2:
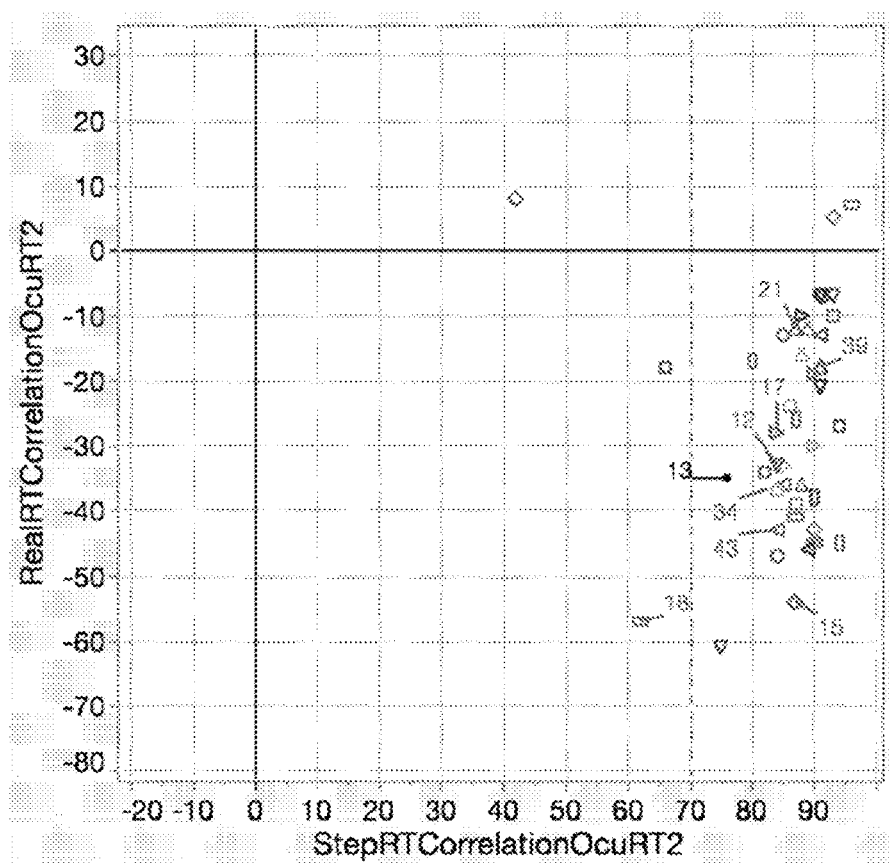
FIG. 2 shows correlations of StepTime of the second OcuRT measurement OcuRT2.

FIG. 2 shows correlation coefficient of the second OcuRT measurement OcuRT2 of each test subjects (n=44) against the total StepTime (x-axis) and individual reaction time (RealRT y-axis). See explanations of FIG. 1 for further explanations.

Figure 3:
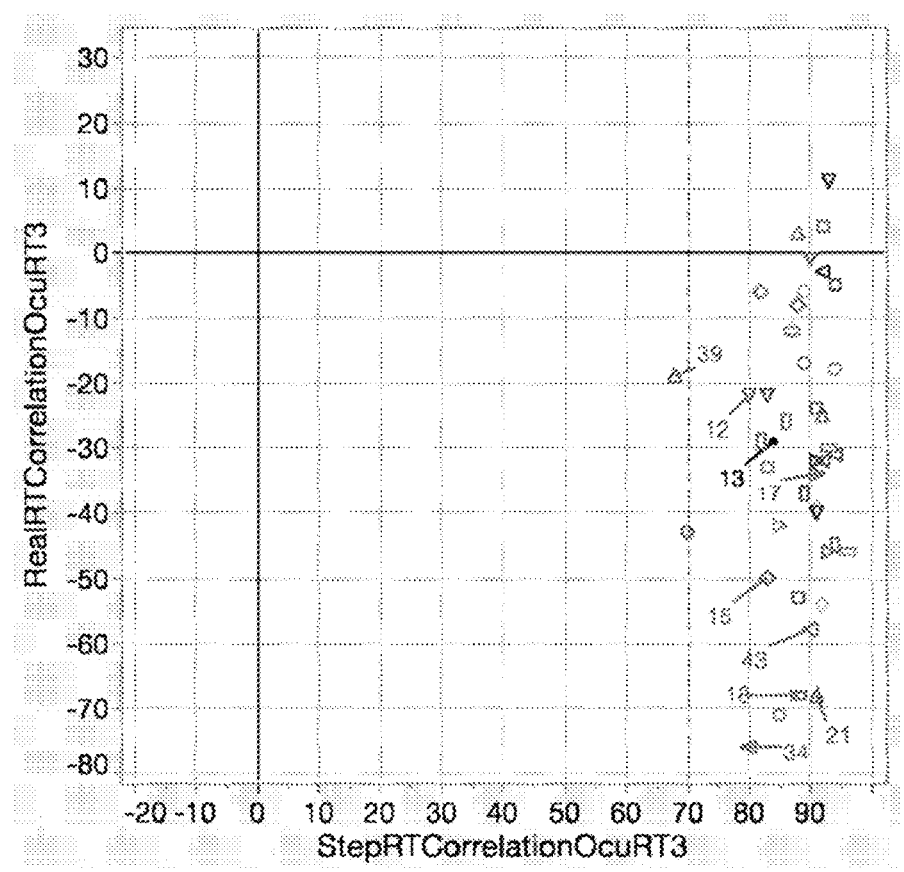
FIG. 3 shows correlations of StepTime of the third OcuRT measurement OcuRT3.

FIG. 3 shows correlation coefficient of the third OcuRT measurement OcuRT3 of each test subjects (n=44) against the total StepTime (x-axis) and individual reaction time (RealRT y-axis). See explanations of FIG. 1 for further explanations.

FIGS. 1 to 3 show that practicing the OcuRT test helped to gain shorter reaction times. In repeated measurements the mean reaction time of the study group with correlation above 70% was about 8 ms better compared to previous measurement (OcuRT1 460.6 ms; OcuRT2: 451.7 ms; OcuRT3: 443.4 ns).

Figure 4:
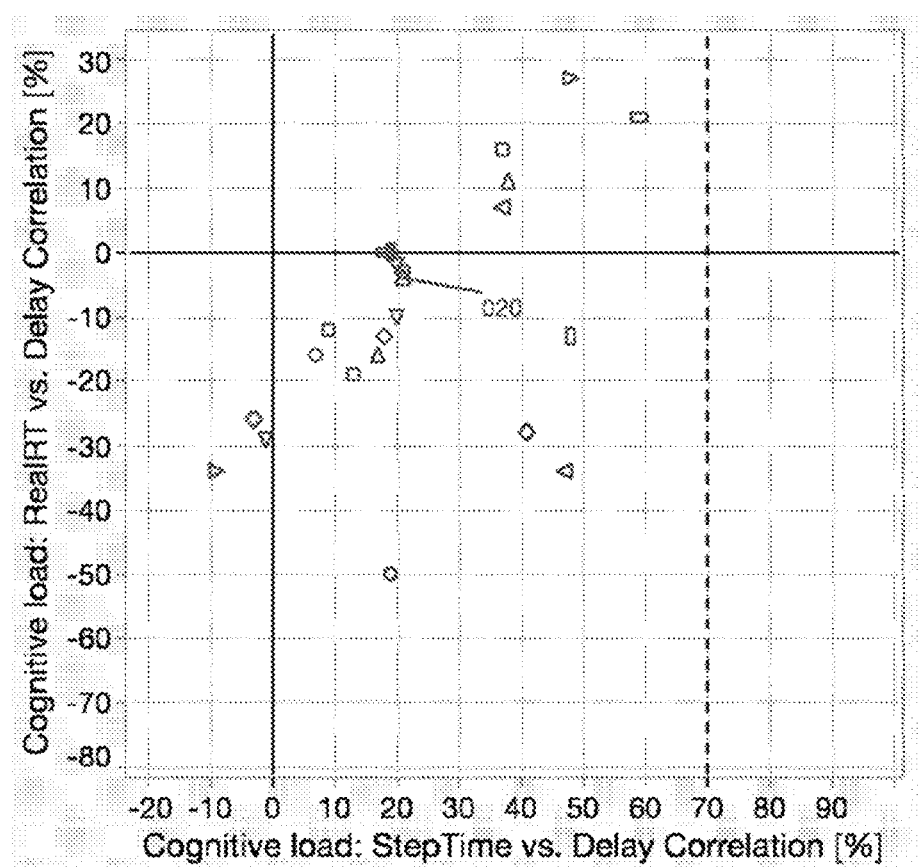
FIG. 4 shows correlations of OcuRT test during added cognitive load.

If the person is not fully attending to the appearance of test stimulus and to the recognition and reporting of its direction by a button press, he is likely to be late in his reactions. In order to make it even more difficult to concentrate to the OcuRT test, cognitive load for the test subjects were increased by telling them to count down from 200 by 7's while they were doing the reaction time test. In FIG. 4 we can see that all test subjects had low StepTime correlations showing inability to simultaneously concentrate to the counting and the appearance of the test stimulus. None of the test persons could achieve high StepTime correlations the maximum being 59% and mean 23.7%.

Figure 5:
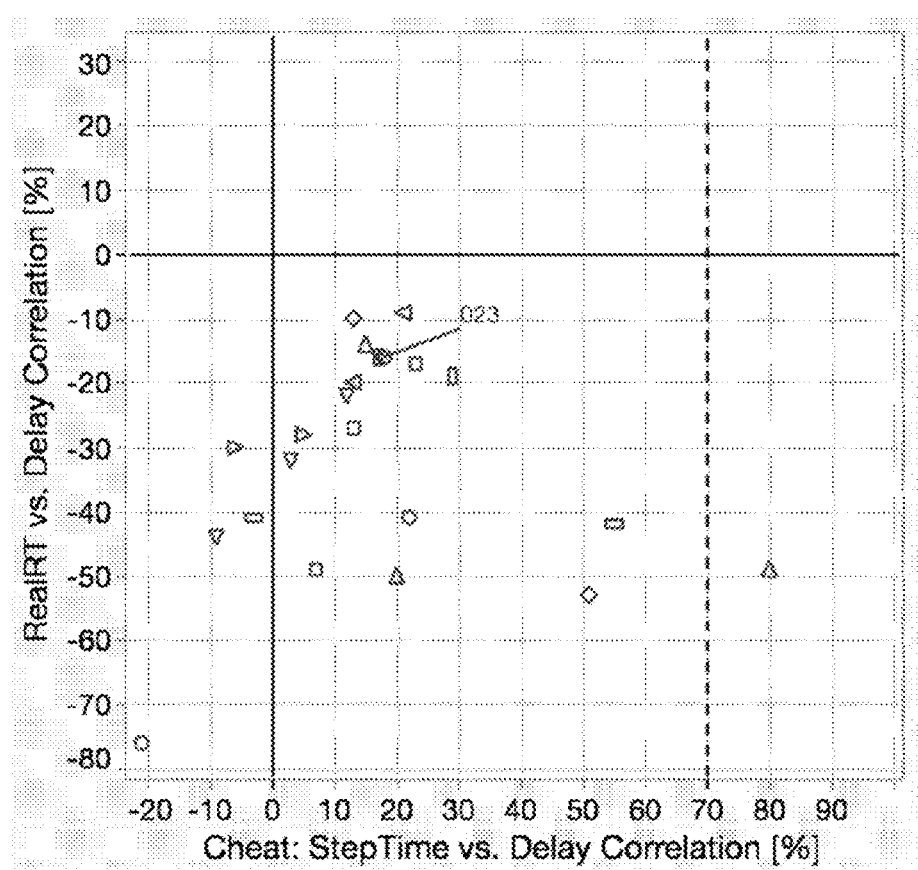
FIG. 5 shows correlations of OcuRT test during deliberate cheating.

FIG. 5 shows correlations of OcuRT test during deliberate cheating. Test subjects answered slowly but in a plausible way trying to cheat money out of the insurance company by malingering of having brain damage caused by head trauma. In the results illustrated in FIG. 5 we can see that only one test subject could achieve high StepTime correlation score (80%) and the other were concentrating rather on the cheating than on the visual reaction time test.

Results from FIGS. 1 to 5 show that the correlation coefficient ST/OT clearly separates the OcuRT measurements which were done with the attentional resources fully aimed towards the appearance of test stimulus and to the recognition and reporting of its direction by a button press as soon as possible. Non-familiarity of the test, thinking of cheating or trying to make difficult mathematical calculations at the same time dearly lowers the StepTime correlation coefficient. Cut off value of 70% based on the visual inspection of the graphs above seems to be a marker for a reliable OcuRT test.

Example 2: Examples for OcuRT Test Algorithm

Figure 6:
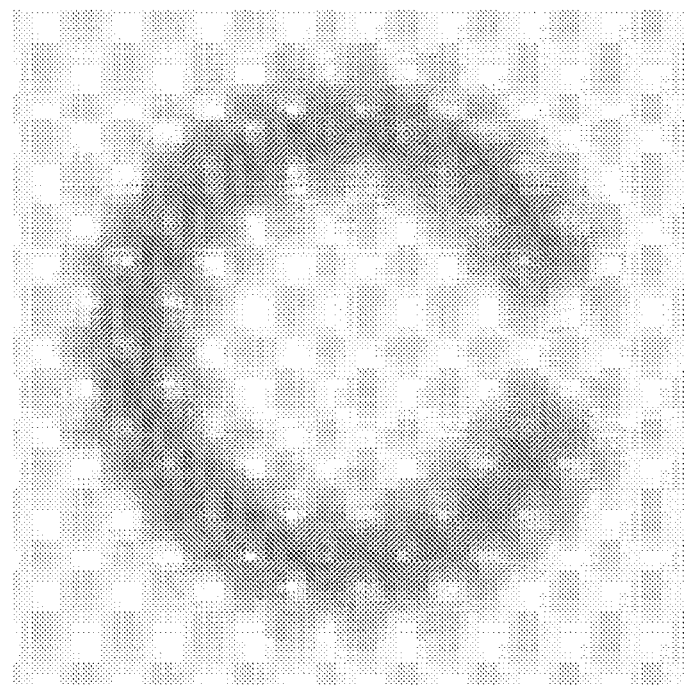
FIG. 6 shows an example of a softened standard Landolt-C.

A few possible examples for the OcuRT are as follows:

Left and right direction images or optotypes, such as standard Landolt-C, may be used as visual test stimuli. One example, a softened standard Landolt-C directed to the right, is shown in FIG. 6.

After each correct response by the test user, the visual test stimuli may by slightly moved on the screen, so that it will be more difficult for the user to make conclusions from "movement" of the test image direction.

Figure 7:
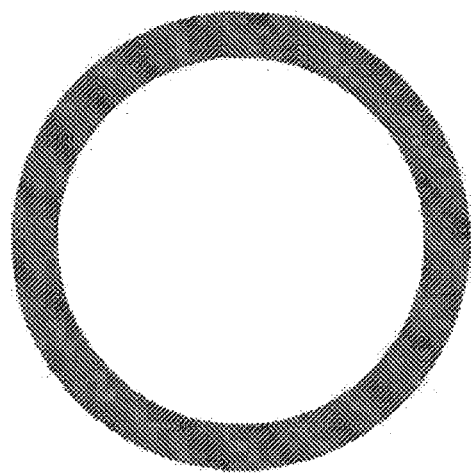
FIG. 7 shows an example of a Wrong response indicator image.

If the test subject responds with a wrong response, e.g. presses a button with a wrong direction, a wrong response indicator image may be shown in place of the test image. The wrong response indicator image may be shown e.g. for 1 to 3 seconds, or for 2.5 seconds. An example of a wrong response indicator image, a ring, is shown in FIG. 7. The ring maybe e.g. red.

The response waiting timeout time may be set e.g. at 2 to 5 seconds, e.g. at 4 seconds. If the test user does not respond within this timeout, the algorithm may interpret that the test user did not see the optotype. It an embodiment it is not interpreted as an error if the test subject does not respond during the timeout time, but the red error ring may still be shown.

There may be a spoken countdown (3-2-1) before the test starts. During this countdown, images, such as black rings may be shown. Time between the countdown numbers can be e.g. between 1 and 3 or around 2 seconds. After countdown, the test subject starts recognizing the visual test stimuli and reports i.e. answers e.g. by pressing left or right button for each image.

A test may comprise a plurality of rounds, e.g. 3. End criterion for a round may vary. It may e.g. be that there are 6 correct answers in a row in 15 steps. And possible, if there are not, the round will be continued until there are 4 correct answers in a row or a maximum number of steps, e.g. 30 during one test round is reached. Immediately after a round ends the countdown for the next round will be started. After e.g. three rounds, the test will be stopped.

Final reaction time can be calculated e.g. as the fastest median from fastest 6 or 4 correct responses in a row. The final result is considered to be reliable, when the error percent in reporting is below a certain limit, e.g. 15%. After the test ends the final results are displayed to the user. The results may show e.g. reaction time, test duration and calculated error percentage from the round whereof the reaction time is calculated.

The background light level may be measured with ambient light sensors and if the light level reaches a predetermined stop value, such as 200 cd/m2, the test is stopped.

The figures and examples show only a few preferred embodiments according to the Invention. Facts of secondary importance with regards to the main idea of the invention, facts known as such or evident for a person skilled in the art are not necessarily discussed. It is apparent to a person skilled in the art that the invention is not limited exclusively to the examples described above, but that the invention can vary within the scope of the claims presented below. The dependent claims present some possible embodiments of the invention, and they are not to be considered to restrict the scope of protection of the invention as such.

The invention claimed is:

1. A method for evaluating reliability of results in a visual reaction test taken by a test user, the method comprising at least the following steps:
   starting the test;
   repeating multiple test steps until a stop criterion is fulfilled, a single test step comprising following phases:
   1) selecting a delay time of the step DT(Step), which is varied between steps;
   2) not producing a visual test stimulus to be recognised for the delay time of the step;
   3) producing a visual test stimulus, at a stimulus time-point of the step STP(Step);
   4) receiving, when reported by the user, the recognition of the stimulus, at a reporting time-point of the step RTP(Step);
   5) beginning a new test step by returning to phase 1), until a stop criterion for the test is satisfied;
   the method further comprising:
   calculating:
   reaction time of a step RT(Step) as time elapsed between the stimulus time-point of the step and the reporting time-point of the step, such that RT(Step)=RTP(Step)-STP(Step) and
   step time of a step ST(Step) as sum of the delay time of the step and the reaction time of the step, such that ST(Step)=DT(Step)+RT(Step);
   determining correlation between step times and delay times or correlation between reaction times and delay times of each test step;
   comparing the determined correlation with predefined correlation values for reliability and thereby determining level of reliability of the results and consistency of test subject's responses.

2. A method according to claim 1, further comprising:
   determining correlation between step times and delay times and correlation between reaction times and delay times of each test step;
   comparing the determined correlations with predefined correlation values for reliability and thereby determining level of reliability of the results and consistency of test subject's responses.

3. A method according to claim 1, further comprising:
   providing a fake stimulus or another stimulus not meant to be recognised in the test during the delay time of the step.

4. A method according to claim 1, wherein correlations are calculated from a limited set of steps selected from the group consisting of from only those where the stimulus was correctly recognized, and from only those where reaction time RT(Step) or step time ST (Step) or delay time DT (Step) fulfils specific criteria.

5. A method according to claim 1, wherein reliability of responses during the test, or during a subset of test steps, is further determined by number of incorrect answers in relation to correct answers.

6. A method according to claim 1, wherein the reported actual reaction time RT of the test subject is determined by using the fastest subset segment of test steps by dividing the step series to sub-blocks and selecting the fastest reliable sub-block in order to reach a better test-retest repeatability.

7. A method according to claim 1, further comprising:
   determining for all test steps or for any subset of test steps, a correlation coefficient ST/DT(Step) between the step time and the delay time of the step;
   comparing the calculated correlation coefficients with predefined values for reliability and thereby determining level of reliability of the results and consistency of test subject's responses.

8. A method according to claim 1, further comprising
   producing the visual test stimulus with a property having a visually recognizable value; and
   receiving, when reported by the user, the recognition of the value of the stimulus property.

9. A method according to claim 8, further comprising
   selecting the value of the visual test stimulus property from a group of at least two different values.

10. A method according to claim 9, wherein the group of at least two different values comprises values "left" and "right".

11. A method according to claim 1, wherein reporting by the user is done by selecting and pressing a reporting button.

12. A method according to claim 11, wherein the user selects the button from a group of at least two different reporting buttons, whereby each button is associated with one possible value of the stimulus property.

13. A method according to claim 1, wherein the visual test stimulus comprises a symbol having a visually recognizable value indicating a direction.

14. A method according to claim 1, wherein the test user reports the visual test stimulus or value of the visual test stimulus property by push-buttons, touch elements, moves of body or body parts, eye movements, oral feedback, magnetic or electrical signal from brain or neural system.

15. A method according to claim 1, wherein the test user's incorrect recognitions of the visual test stimulus produce feedback or sign for the test user, indicating wrong response, thus encouraging the test user to respond correctly.

16. A method according to claim 1, further comprising producing the visual test stimulus on an electronic screen.

17. A method according to claim 16, wherein, if a visual test stimulus was correctly recognised, the next visual test stimulus is produced on a different location on the screen.

18. A method according to claim 1, wherein the stop criterion is satisfied when a number of successive steps where the stimulus was correctly recognised is recorded, the number being from 3 to 10.

19. A method according to claim 1, further comprising
   varying the delay time of the step randomly or by any predefined sequence or by an algorithm between a lower limit and a higher limit of the delay time.

20. A method according to claim 19, further comprising
   changing the lower limit and/or the higher limit of the delay time between the test steps according to observed reaction times of the user, or according to other predefined criteria.

21. A method according to claim 19, further comprising selecting the lower limit to be between 50 and 500 ms, and selecting the higher limit to be between 200 and 1000 ms.

22. A method according to claim 1, wherein
   reaction times of steps with shorter delays are summed, averaged, or otherwise bundled together as RT(ShortDelays), and separately of that,
   reaction times of steps with longer delays than the ones bundled to RT(ShortDelays) are summed, averaged, or otherwise bundled together as RT(LongDelays), and
   the absolute values of the RT(ShortDelays) and RT(LongDelays) or difference or relation of these are used to further analysis to determine how well the concentration of the test user recovers from reporting task of the previous step, using a relation between RT(SHortDelays) and RT(LongDelays), or what is the test user's reaction time without impact of previous step.

23. A method according to claim 1, wherein in order to determine the minimum time a person needs for recovery from a previous step in order to be attentive to the new stimulus, the delay time is shortened until reaction time begins to slow down.

24. A system for evaluating reliability of results in a visual reaction test taken by a user comprising
- a computer with a memory;
- a computer program runnable on the memory, the program comprising program code elements adapted to perform and control the visual reaction test;
- a display device arranged show a visual test stimulus as instructed by the computer program;
- reporting device arranged to receive a recognition of the stimulus by the user and arranged to transfer information of said recognition to the computer;

wherein the program code elements are adapted to perform method steps according to claim 1.

* * * * *